United States Patent [19]

Soifer

[11] Patent Number: 4,488,874
[45] Date of Patent: Dec. 18, 1984

[54] DETACHABLE MOUNTING FOR A DENTAL FIXTURE AND METHOD FOR USING SAME

[76] Inventor: Jack Soifer, 287 Park Ave., Rochester, N.Y. 14607

[21] Appl. No.: 536,191

[22] Filed: Sep. 27, 1983

Related U.S. Application Data

[63] Continuation-in-part of Ser. No. 373,264, Apr. 29, 1982, abandoned.

[51] Int. Cl.³ ............................................. A61C 8/00
[52] U.S. Cl. ..................................... 433/173; 433/177
[58] Field of Search ................ 433/213, 173, 177, 220

[56] References Cited

U.S. PATENT DOCUMENTS

| | | | |
|---|---|---|---|
| 711,324 | 10/1902 | Lacy | 433/173 |
| 2,691,219 | 10/1954 | Sandri | 32/5 |
| 2,746,149 | 5/1956 | Del Papa | 32/10 |
| 3,328,879 | 7/1967 | Bax | 32/12 |
| 3,797,114 | 3/1974 | Wiland | 32/12 |
| 4,193,194 | 3/1980 | Dalise | 433/177 |
| 4,204,321 | 5/1980 | Scott | 433/177 |
| 4,362,511 | 12/1982 | Jacklich | 433/220 |

OTHER PUBLICATIONS

Two trade pamphlets distributed by Bell International, entitled "Precision Attachment", (two pages), and Instructions and Use of ASC-SR Attachment, (six pages).
Two trade pamphlets distributed by CEKA, p.v.b.a. (through Pennwalt-Jelenko), entitled "What Every Dentist Should Know About the CEKA Anchor System", In Relation to Intra-Coronal and Extra-Coronal CEKA Anchors, (two pages each).
A trade pamphlet distributed by Jodent Products, Inc., entitled "Jodent/ddi Attachments", (two pages).
A trade pamphlet distributed by Scodenco, entitled "Scodenco's New O-SO ™ Attachment System", (four pages).
A sheet of trade literature entitled "Universal Attachment—The Extraordinary Extracoronal Attachment", (2 sides).
A sheet of trade literature distributed by Whaledent International, bearing a distribution No. D2.7.
An article entitled "Precision Attachments in Partial Dentures . . . Gentler on Abutments. More Aesthetic Than Clasps", including illustrations, (two pages).
A Product Report taken from p. 16 of "Modern Dentalab", describing four separate attachment constructions.
A sheet of trade literature describing and illustrating a SANDRI stud-type overdenture attachment.
Two trade pamphlets distributed by CEKA, p.v.b.a. entitled "CEKA Attachment Laboratory Procedures", (two pages), and CEKA Lab Procedure, (two fold-out pages).
Four sheets of trade literature illustrating and describing Dalla Bona Radicular Telescopic Stud Attachments and their method of use and installation.
Two sheets of trade literature illustrating and describing Gerber Radicular Telescopic Stud attachments and their method of use and installation.
Four sheets of trade literature illustrating and describing Rothermann Radicular Telescopic Stud attachments and their method of use and installation.
An information sheet distributed by Whaledent International, entitled "Precision Attachments", (eight pages).
An article entitled "Prefabricated Precision Attachments for Overdentures", published in *The Bulletin*, Mar., 1976, (two pages).

*Primary Examiner*—Robert Peshock
*Attorney, Agent, or Firm*—Ruth Moyerman

[57] ABSTRACT

A device for use in attaching a dental prosthesis to a tooth, comprising cooperating male and female portions having a base and a head, respectively, for attachment to and between the dental prosthesis and the tooth, and a post assembly forming part of the male portion and comprising a base member adapted for attachment to the base of the male portion and having an aperture extending through central portions thereof, a stud extending through the aperture of the base member and having one end which is rotatingly associated with the base member, an engagement member attached to another end of the stud and adapted for engagement with a retention device associated with the female portion, and a resilient washer surrounding the stud and separating the base member from the engagement member. Also, a method for attaching a dental prosthesis to a tooth.

21 Claims, 10 Drawing Figures

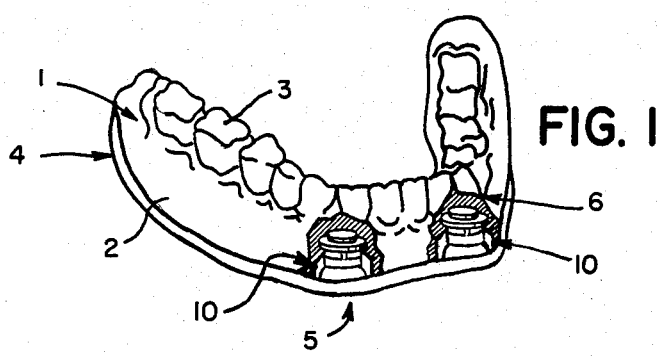
FIG. 1
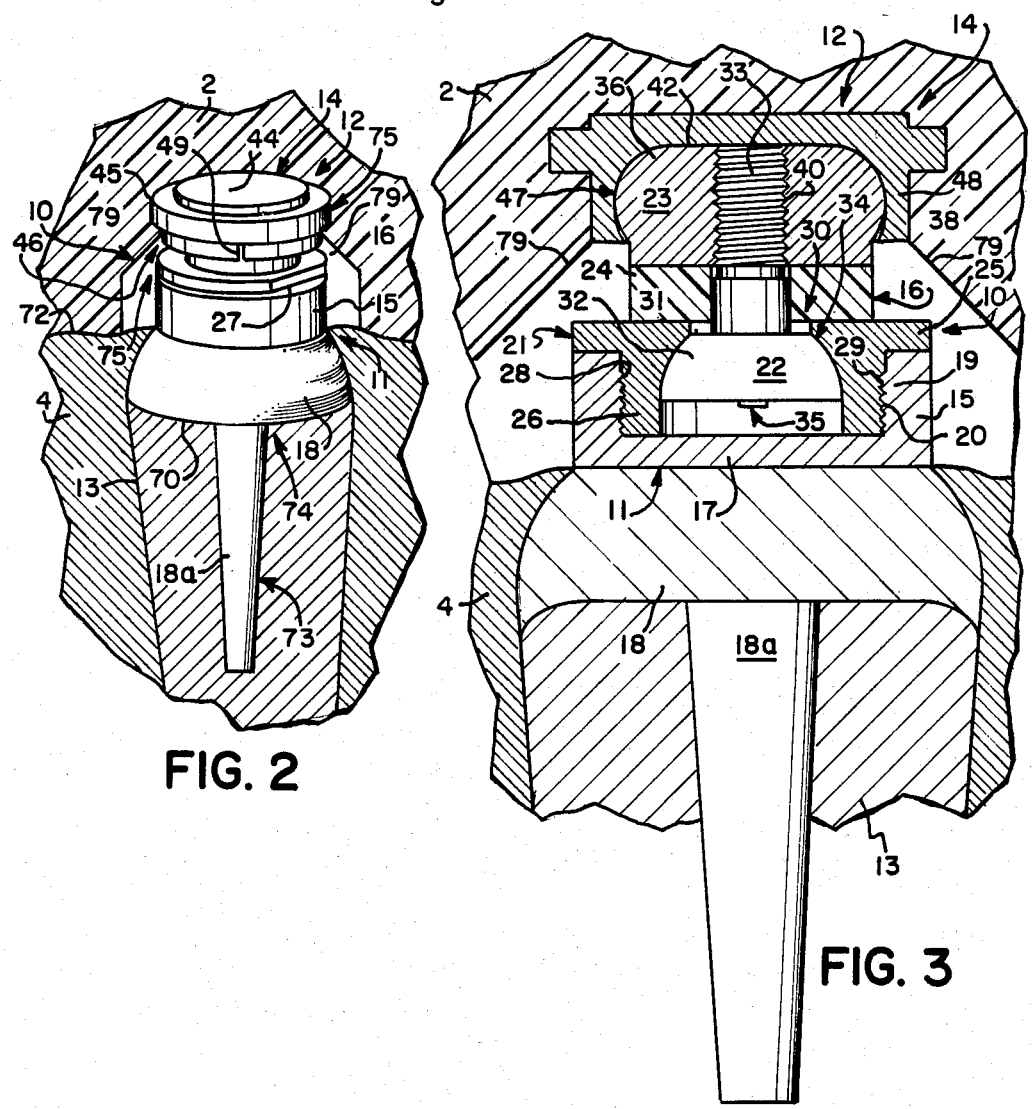
FIG. 2
FIG. 3

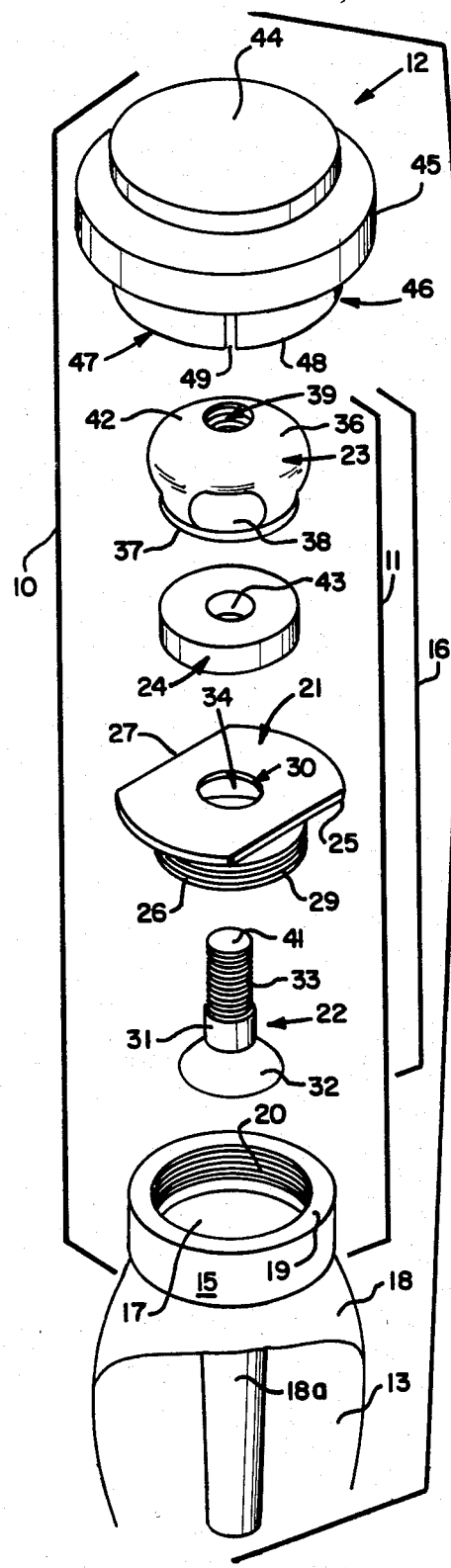
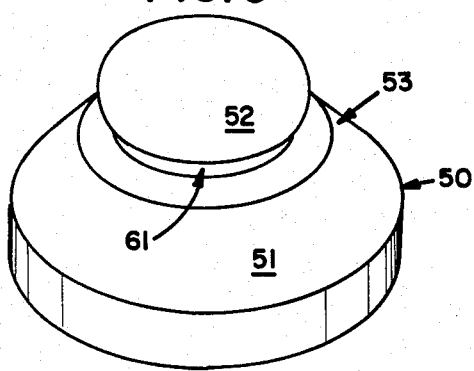
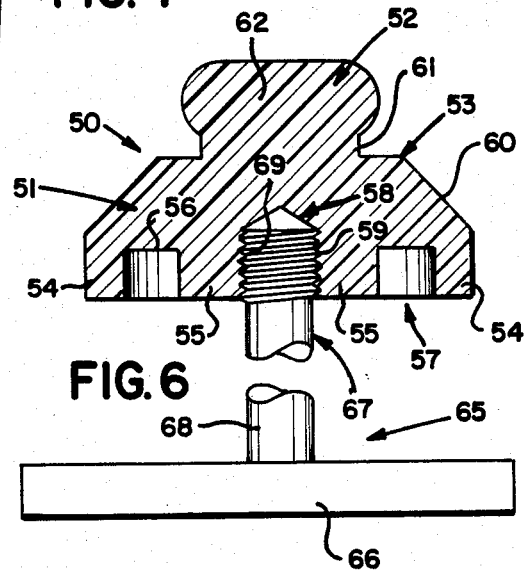
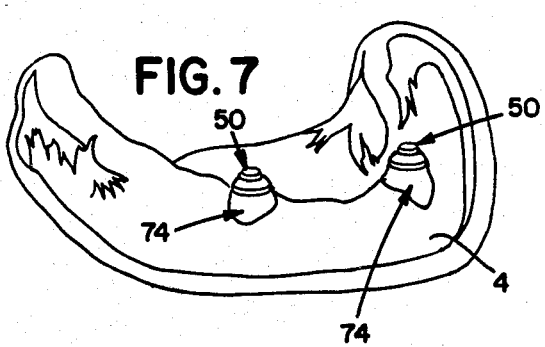

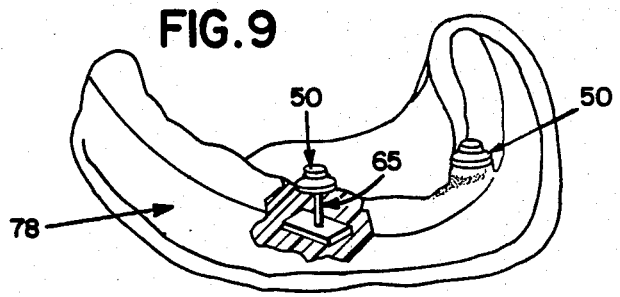
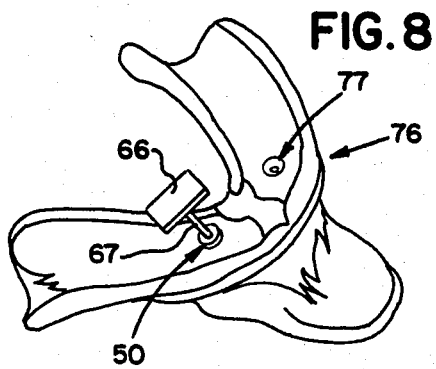
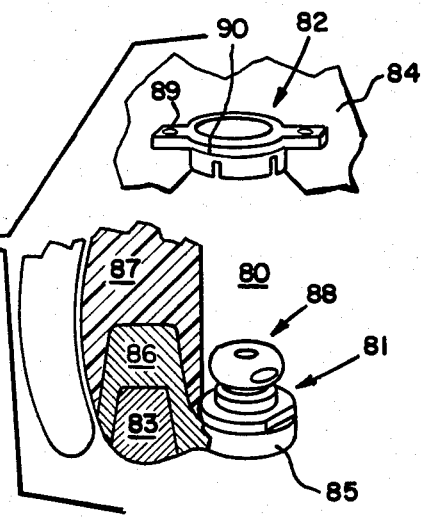

DETACHABLE MOUNTING FOR A DENTAL FIXTURE AND METHOD FOR USING SAME

RELATED CASE

The present application is a continuation-in-part of my prior copending U.S. patent application Ser. No. 373,264, filed Apr. 29, 1982 and now abandoned, the subject matter of which is incorporated by reference as if fully set forth herein.

BACKGROUND OF THE INVENTION

The present invention relates generally to detachable mountings for dental prostheses, and more particularly, to a system for denture retention.

Many applications call for the use of dental fixtures (either full or partial) to reestablish normal anatomical movement, to stimulate normal and natural chewing during mastication of food, as well for various cosmetic reasons. In connection with such restorations, it is clearly important that the dental fixture be securely retained in position, easily serviceable, and comfortable in use. A variety of detachable mounting devices have therefore been developed to detachably retain a dental fixture within the mouth of a patient in a manner which provides these functions.

One such attachment device which has found general acceptance is the intra-coronal attachment. Generally, such an attachment will incorporate a cooperating male and female portion. The male portion is generally associated with one or more prepared teeth remaining available in the patient's mouth. The female portion is generally associated with the dental fixture and is located for alignment with the male portion upon subsequent attachment. The number of cooperating male and female portions used will, of course, depend upon the application. Generally, only one or two such male-female combinations are used. In use, the dental fixture is secured in position by merely snapping the female portion over the male portion (or portions), removal of the dental fixture being accomplished by reversing this procedure.

Another type of attachment was has found general acceptance is the extra-coronal attachment. Again, cooperating male and female portions are provided, one portion generally being associated with available feeth remaining in the patient's mouth, and the other portion generally being associated with the dental fixture. However, unlike intra-coronal attachments, which are generally used in connection with full restorations, extra-coronal attachments are used in conjunction with the remaining teeth, and are therefore generally used in connection with partial restorations.

Although the foregoing attachment methods have found general acceptance and provide adequate results, several difficulties remain which are capable of improvement.

For example, to securely retain the dental fixture in position, such attachments must generally develop a relatively tight fit between associated male and female portions. Unfortunately, this also prevents relative movement between the dental fixture and the portions of the user's mouth to which it is attached, even when such movement would be desirable. Often, no provisions are made for such movement. This can lead to relatively minor difficulties such as unwanted detachment of the dental fixture, or more serious difficulties such as damage to the dental fixture, the attachment, or even portions of the teeth which anchor the attachment. Particularly in the latter case, this can result in serious damage which is costly to repair, if repair is even possible.

Difficulties also often arise in assuring correct alignment between the portions of the attachment which are secured to the patient's teeth, and the portions of the attachment which are associated with the dental fixture. Clearly, it is important that these respective structures be correctly positioned to assure that the dental fixture is correctly aligned within the mouth of the patient. However, the alignment procedures which are generally required to achieve this result often necessitate the expenditure of a significant amount of time on the part of the dentist performing the installation to assure correct placement, significantly increasing the cost of such dental work.

It therefore remains desirable to develop a detachable mounting device which serves to overcome the foregoing disadvantages.

SUMMARY OF THE INVENTION

It is therefore a primary object of the present invention to provide an improved detachable mounting device for use in connection with dental fixtures.

It is also an object of the present invention to provide a detachable mounting device for use in connection with dental fixtures which permits relative movement between the dental fixture and the portions of the mouth of the patient to which it is attached.

It is also an object of the present invention to provide a detachable mounting device for use in connection with dental fixtures which reduces stress to the tooth receiving the mounting device.

It is also an object of the present invention to provide a detachable mounting device for use in connection with dental fixtures which permits relative movement between the dental fixture and the portions of the mouth of the patient to which it is attached, both horizontally and vertically.

It is also an object of the present invention to provide a detachable mounting device for use in connection with dental fixtures which is easily installed, used and serviced.

It is also an object of the present invention to provide a means for facilitating the installation of a detachable mounting device having the foregoing capabilities.

It is also an object of the present invention to provide a method for installing a detachable mounting device having the foregoing capabilities, one which requires a minimal amount of intervention on the part of the dentist during the installation procedure.

These and other objects are achieved by providing an attachment device for use with a dental fixture which generally comprises a male portion capable of engaging portions of a tooth and formed in accordance with the present invention, and a cooperating female portion capable of association with the dental fixture and formed in accordance with the present invention.

The male portion generally comprises a base for engaging the portions of the tooth which will serve as the anchor for the resulting assembly, and a post assembly threadingly engaging the base. The post assembly includes a threaded base portion having a centrally disposed aperture; a stud extending through the aperture of the base portion; a male member engaging terminal portions of the stud; and a resilient washer surrounding the stud and positioned between the male member and the base portion of the post assembly.

The female portion generally comprises a flanged head having means for engaging the male member of the post assembly. The flange of the female portion is capable of being enclosed within the dental fixture during its manufacture.

In use, the base is attached to a tooth which will serve to anchor the resulting assembly in conventional fashion, and the several components comprising the post assembly are assembled and threadingly attached to the base. Installation of the dental fixture is achieved by snapping the cooperating female portion over the male member of the post assembly, detachment being accomplished by reversing this procedure. Both horizontal and vertical movement of the dental fixture are accommodated by the resilient washer and cooperation between the stud and the base portion of the post assembly which engages it.

The foregoing assembly is enhanced by an improved method for installing and aligning the foregoing structures, which makes use of a novel locator and positioner assembly. The locator is essentially used to simulate the post assembly of the male portion, while the positioner is used to simulate the location of the post assembly in the patient's mouth. These components are capable of use in connection with procedures which are conventionally used to manufacture dental fixtures to assure that, during manufacture, the female portion associated with the dental fixture is correctly aligned with the male portion associated with the patient's tooth in a manner which minimizes the amount of time which a dentist must expend to achieve this result.

Further detail regarding the attachment device of the present invention is provided in the following detailed description of a preferred embodiment of the present invention, with reference to the following illustrations.

BRIEF DESCRIPTION OF THE DRAWINGS

FIG. 1 is a perspective view illustrating use of the detachable mounting device of the present invention, portions of which have been removed to show internal construction detail.

FIG. 2 is a partial, enlarged perspective view of the detachable mounting device illustrated in FIG. 1, also showing portions of the associated post crown and dental fixture.

FIG. 3 is a cross-sectional view of the structure illustrated in FIG. 2.

FIG. 4 is an exploded view of the structure illustrated in FIG. 2.

FIG. 5 is a perspective view of a locator/adapter which can be used in connection with the detachable mounting device of the present invention to facilitate manufacture and installation of the dental fixture.

FIG. 6 is a cross-sectional view of the locator/adapter illustrated in FIG. 5, also showing an associated positioner which is used in connection therewith.

FIG. 7 is a perspective view illustrating placement of the locator/adapter of FIG. 5 in connection with the base of the male portion of the detachable mounting device of the present invention.

FIG. 8 is a perspective view illustrating placement of the adapter and associated positioner in connection with an impression of the structure illustrated in FIG. 7.

FIG. 9 is a perspective view illustrating a model formed from the impression illustrated in FIG. 8.

FIG. 10 is a partial, exploded perspective view illustrating an extra-coronal attachment formed in accordance with the present invention, portions of which have been removed to show internal construction detail.

In the several views provided, like reference numerals denote similar structure.

DETAILED DESCRIPTION OF THE PREFERRED EMBODIMENT

Although specific forms of the invention have been selected for illustration in the drawings, and the following description is drawn in specific terms for the purpose of describing these forms of the invention, this description is not intended to limit the scope of the invention which is defined in the appended claims.

FIG. 1 generally illustrates placement of a completed dental fixture such as the denture 1 within the mouth of a patient (not shown). The denture 1 generally includes a simulated gum portion 2 and a plurality of simulated teeth 3 projecting therefrom, as is conventional. Using conventionally available manufacturing materials and techniques, it will be understood that the gum portion 2 of the denture 1 will be configured to correspond to the patient's gums 4 to form an assembly which is comfortable to wear and natural in appearance.

Of course, it is also important that appropriate attachments be provided to securely retain the denture 1 in position. In the embodiment selected for illustration in the drawings, two points of attachment 5, 6 have been selected. This is generally perferred when available material exists for the development of two such points of attachment. Of course, it will be understood that other applications may call for a different numer of attachment points, since many times only one secure point of attachment remains available for use. It will therefore be understood that the attachment means of the present invention will find applicability in connection with any number of available points of attachment, as will be more fully described below, and that the embodiment selected for illustration in the drawings is merely representative of possible applications of the attachment means of the present invention.

FIG. 2 illustrates structure located in the vicinity of one of the attachment points, at 5, in greater detail. Securing the denture 1 to the patient's gums 4 in the vicinity of the attachment point 5 is an attachment means 10 formed in accordance with the present invention. The attachment means 10 generally comprises a male portion 11 and a cooperating female portion 12. The male portion 11 is secured to a tooth 13 remaining available in the patient's mouth. In this regard, an available tooth is taken to mean an appropriate tooth which retains sufficient structural integrity to recive the structure comprising the male portion 11, and to retain the attachment means 10 and denture 1 in position during use. As previously mentioned, in many applications more than one tooth will remain which is structurally sound and capable receiving an attachment means 10 in accordance with the present invention. Since each such attachment point would be prepared similarly, the following discussion will proceed only in connection with the attachment point 5, it being understood that any other selected attachment points would be prepared similarly.

The female portion 12 is operatively associated with the denture 1, and is located in a cavity 14 of the denture 1 so that, in use, the female portion 12 will be placed in substantial alignment with the male portion 11. From the foregoing, it will be understood that the denture 1 is readily secured over the patient's gums 4 by operatively connecting the male portion 11 and female portion 12. Removal of the denture 1 is accomplished be reversing this procedure.

Referring to FIGS. 3 and 4, the structure comprising the male portion 11 and female portion 12 will now be described in greater detail. The male portion 11 generally includes a base 15 and a post assembly 16. The base 15 is generally cup-shaped, the bottom 17 of the base 15 being adapted for attachment to a crown 18. Associated with the crown 18 is a post 18a adapted for attachment to the tooth 13 as will be more fully described below. The inside of the wall 19 of the base 15 has a plurality of threads 20 for receiving the post assembly 16.

The post assembly 16 generally comprises a base portion 21, a stud 22 extending from the base portion 21 and into engagement with a male member 23, and a resilient washer 24 positioned between the base portion 21 and the male member 23 and surrounding the stud 22.

The base portion 21 generally includes an essentially flat flange 25 and a cylindrical portion 26 depending from the flange 25 as illustrated. The outer wall 28 of the cylindrical portion 26 is provided with a plurality of threads 29 for engaging the threads 20 of the base 15, and the flange 25 is provided with flats 27 to facilitate assembly.

An aperture 30 extends through the center of the flange 25 for receiving the shank 31 of the stud 22. One end of the shank 31 of the stud 22 is provided with a shaped head 32, while the opposing end of the shank 31 is provided with a plurality of threads 33. The head 32 is essentially hemispherical in shape and is configured to substantially correspond to a hemispherical cavity 34 defined beneath the flange 25. These hemispherical structures cooperate to enable rotation of the stud 22 with respect to the base portion 21 as will be more fully described below.

To facilitate assembly of the post assembly 16, the head 32 of the stud 22 is provided with a fitting 35 for receiving a corresponding tool (not shown) capable of enabling the stud 22 to be rotated and tightened. In the present embodiment, the fitting 35 is an Allen fitting capable of receiving a conventional Allen wrench. Of course, fittings and tools having other configurations could be used if desired.

The male member 23 includes an oval or donut-shaped ball member 36 having a substantially flat flange 37. Opposing faces of the ball member 36 are provided with flats 38 as shown to facilitate assembly of the post assembly 16, in conjunction with the fitting 35 of the stud 22. An aperture 39 extends essentially centrally through the male member 23, and is provided with threads 40 for receiving and engaging the threads 33 associated with the stud 22. Preferably, the aperture 39 extends fully through the male member 23, and the length of the stud 22 is such that the terminating end 41 of the stud 22 lies essentially flush with the outer face 42 of the male member upon assembly. Of course, this structural relationship will be dependent upon the thickness of the washer 24 selected for use in conjunction with this assembly. Although less preferred in view of the increased manufacturing costs which would result, it is also possible to provide the male member with a centrally disposed aperture which does not fully extend through the male member, but which terminates at a selected distance from its outer face to provide a male member having a solid outer face.

Located between the flange 37 of the male member 23 and the flange 25 of the base portion 21 is the washer 24. The washer 24 is essentially annular in shape and includes an aperture 43 extending through its center. The washer 24 may be formed of any of a variety of resilient materials, particularly those which exhibit a simple hydraulic movement. A variety of flowable rubber materials are capable of providing this function, however, washers 24 formed of silicone materials are preferred. Upon tightening the stud 22 against the male member 23, the washer 24 will be placed in compression. Due to the characteristics of the material forming the washer 24, forces applied against the male member 23 will be accommodated by movement of the male member 23 with respect to the base portion 21, accounting for necessary transient denture motion. This includes both vertical movement resulting from forces applied axially with respect to the post assembly 16, horizontal movement resulting from forces applied transversely to the post assembly 16, as well as combinations thereof. The degree to which such forces are accommodated will depend upon the resiliency (the compression set) of the washer 24, which may be varied to suit a particular application. Preferably, washers of different resiliency will be color coded to facilitate proper selection. In addition to biasing the male member 23 toward a normal position, the washer 24 also serves to absorb developed vibrations.

The female portion 12 generally comprises a head 44, a flange 45 associated with the head 44, and retention means 46 depending from the head 44 as shown. The flange 45 serves to securely retain the female portion 12 within the material forming the denture 1 as will be more fully described below. The retention means 46 cooperates with the head 44 to define a cavity 47 having a configuration which substantially corresponds to the configuration of the ball member 36 of the male member 23. Preferably, the retention means 46 is comprised of a series of depending bands 48 separated by spaced slits 49, as shown, terminal portions of the depending bands 48 extending inwardly to partially restrict the cavity 47 and thereby engage and securely retain the ball member 36 with the cavity 47 upon assembly. Although this structure is preferred to facilitate attachment of the female portion 12 to the male portion 11, as well as to facilitate detachment, other suitable arrangements may be developed to suit a particular application.

Having described the structural features comprising the attachment means 10 of the present invention, its manner of use in connection with an exemplary dental procedure will now be described. In connection with such use, two assembly implements are provided to facilitate manufacture of the denture 1 as will be more fully described below. These include a locator/adapter 50 and a positioner 65.

The locator/adapter 50 generally includes a base portion 51 and a ball member 52 operatively associated with the base portion 51. The base portion 51, which is larger in diameter than base 15, takes, intermediate its ends, the form of a truncated conical member. The ball member 52 is operatively associated with the apex 53 of the base portion 51, and incorporates a spacing flange 61 and a donut-shaped head 62 which essentially corresponds to the shape of the male member 23 associated with the post assembly 16. An annular outer ring 54 and an annular inner ring 55 each depend from the bottom 56 of the base portion 51. The annular rings 54, 55 combine to define a first, annular cavity 57 between the outer ring 54 and the inner ring 55, and an essentially centrally located cavity 58 which is provided with a series of threads 59.

The positioner 65 generally includes a base 66 and a stud 67 operatively associated with the base 66. The base 66 selected for illustration in the drawings is substantially rectangular in shape, however, other shapes may also be used as desired. The shank 68 of the stud 67 is connected to the base 66, and the opposing end of the stud 67 is provided with a plurality of threads 69 capable of receiving the threaded cavity 58 of the adapter 50.

In connection with the exemplary dental procedure which will now be described, it is being assumed that the patient requires a full denture and has two teeth 13 which are structurally sufficient to receive attachment hardware. Accordingly, two separate attachment means 10 will be used in connection with this dental procedure.

Initially, each of the teeth 13 which are to receive an attachment means 10 will be conventionally prepared by removing exposed portions of each tooth to form a prepared surface 70 which will eventually constitute a point of attachment for the denture 1. Generally, this involves the removal of upper portions of each tooth 13 to develop a prepared surface 70 which is located at or near the gum line 72. Thereafter, the centrally disposed cavity 73 will be prepared for receiving appropriate hardware.

After this preparation, a base 15 is attached to each of the teeth 13. This is accomplished by attaching the base 15 to a post and crown assembly 74 configured to engage the cavity 73 in conventional manner. The base 15 and assembly 74 may be attached either by soldering the components together, or casting the components as a unit. In this regard, it should be noted that the threads 20 of the base 15 will conveniently accept either a paralleling mandrel or a soldering mandrel to facilitate this process. In either case, the resulting assembly is then appropriately affixed over the prepared surface 70, for example, using a conventional dental cement. This will place the bottom 17 of the base 15 in contact with crown 18, the crown 18 in contact with the prepared surface 70, and the post 18a within the cavity 73, providing a secure basis for the remainder of the dental procedure.

To arrange for the manufacture of a suitable denture 1 which is correctly sized in relation to the patient, it is generally necessary to take an impression of the patient's mouth. In accordance with the present invention, and with reference to FIG. 7, this impression is taken in connection with the locator/adapter 50 previously described to essentially record the location of the male portion 11 and to facilitate correct manufacture of the denture 1 as will be more fully described below.

As previously described, the adapter 50 includes an annular cavity 57 associated with the base portion 51. This annular cavity 57 is configured to cooperate with the base 15 which is attached to the post and crown assembly 74 by receiving and engaging the wall 19 of the base 15. This engagement may either be frictional, developing a press-fit arrangement, or the adapter 50 may be formed of a material which enables the inner ring 55 to threadingly engage the base 15 at the threads 20. Regardless of the engagement developed, the adapter 50 is easily placed in position over the wall 19 of the base 15, developing the following measurements. First, as a result of its construction, the ball member 52 of the adapter 50 will correspond in size and location to the ball member 36 of the male member 23 which will subsequently form part of the post assembly 16. Second, as a result of its construction, the base portion 51 of the adapter 50 will establish a cavity 75 (FIG. 2), for enabling and assuring correct movement of the ball member 36 during use. Thus, when the impression is taken, the base portion 51 and ball member 52 associated with the adapter 50 will automatically establish voids to facilitate the remainder of the dental procedure, as will be more fully described below, simply by placing the adapter 50 over the base 15 as previously described. After placement of the adapter 50 over the base 15, an impression of the structure illustrated in FIG. 7 is taken in conventional manner.

FIG. 8 illustrates the resulting impression 76. It will be noted that the impression 76 includes two voids 77 which correspond in location to each base 15, and in configuration to the adapter 50 associated with each base 15. After formation of the impression 76, each adapter 50 is removed from the base 15 for subsequent use in connection with the impression 76. In doing so, the threaded aperture 58 of the adapter 50 is attached to the stud 67 of the positioner 65. The resulting assembly of the adapter 50 and the positioner 65 will accordingly simulate placement of the adapter 50 in the patient's mouth. This serves to provide an external simulation of the male portion 11.

As is conventional, the impression 76 is used to form a model 78 of the patient's mouth. Prior to formation of the model 78, an assembled adapter 50 and positioner 65 are located in each of the voids 77 developed in the impression 76. This is simply accomplished by pushing the adapter 50 into each void 77 until interaction between the respective structures retains the adapter 50 within the associated void 77. As a result of the resiliency of the material forming the impression 76, the associated positioner 65 will extend outwardly from each void 77 as shown in FIG. 8. As the model 78 is formed, it will be understood that the positioner 65 associated with each void 77 will be surrounded by the material used to form the model. Upon its formation, the model 78 will be removed from the impression 76, the positioner 65 being retained within the body of the model 78, and the adapter 50 extending from the model 78 as illustrated in FIG. 9, providing an accurate means for externally locating each male portion 11 which is to be provided in the patient's mouth.

Thereafter, the model 78 is used to form the denture 1. Previously, such a denture would be formed with enlarged voids or cavities in the vicinity of the region which would subsequently receive the female portion of the attachment. Actual encasement of the female portion of the attachment would be performed by the dentist, after delivery of the denture, to assure proper location of the female portion with respect to its male counterpart.

The present invention essentially eliminates the need for this operation as follows. As previously mentioned, the model 78 formed in accordance with the present invention includes an adapter 50 representing the correct location of each male portion 11 in the patient's mouth. In fact, the ball member 52 associated with the adapter 50 corresponds in location to the male member 23 which will subsequently form the post assembly 16. Accordingly, placing the female portion 12 over the ball member 52 of the adapter 50 prior to formation of the denture 1 will establish correct location of the female portion 12 in relation to the patient's mouth. The denture 1 can then be formed in connection with the model 78 using conventionally available techniques, however, rather than providing enlarged voids for subsequently receiving a female member, the denture 1 can be completely formed with each female portion 12 correctly encased therein. The cavity 75 which will subsequently receive the post assembly 16 and assure correct movement of the associated male member 23 will also be developed as a result of the base portion 51 of the adapter 50. The resulting denture 1 will therefore be completed and ready for installation by the dentist, without requiring subsequent adjustment and placement of female portions as previously required.

In connection with this process, it is generally preferred that the retention means 46 associated with each female portion 12 be appropriately covered to prevent the material forming the denture 1 from entering the slits 49 associated with the retention means 46, as well as the cavity 47. A variety of methods may be used in this regard, including the placement of a sleeve (preferably teflon) about the retention means 46, the placement of shrink tubing about the retention means 46, or the placement of an insulating paste over the slits 49.

To enable attachment of the completed denture 1, all that remains is to complete assembly of the male portion 11. To do so, the post assembly 16 must first be formed. In connection with this, the dentist would select or prescribe a washer 24 having an appropriate compression set. Thereafter, the dentist, or preferably a technician, would complete the post assembly 16 by extending the stud 22 through the base portion 21 so that the head 32 of the stud 22 is located within the cavity 34 of the base portion 21, placing the prescribed washer 24 over the exposed shank 31 of the stud 22, and threadingly connecting the male member 23 to the free end of the stud 22. The resulting assembly is then tightened until the washer 24 is placed in correct compression, using an appropriate tool to engage the fitting 35 and an appropriate wrench to engage the flats 38 of the male member 23. The prepared post assembly 16 can then be supplied to the dentist together with the completed denture 1.

Upon receiving the completed denture 1 and the assembled post assembly 16, the remainder of the installation process performed by the dentist is straightforward and essentially mechanical. First, the post assembly 16 is connected to the base 15 and tightened in place using an appropriate wrench engaging the flats 27 of the base portion 21. The flange 25 may be flared adjacent the flats 27 to facilitate engagement by the wrench used. Finally, the denture 1 is simply snapped into position, any female portions 12 provided engaging their male counerparts.

In connection with the foregoing, it will be noted that many of the procedures which traditionally had to be performed in the patient's mouth have now been replaced with procedures which may be performed externally. This enables much of the work previously performed by the dentist to be delegated to appropriate technicians. Essentially, the only procedures which must still be performed by the dentist are installation of the post and crown assembly 74 with the base 15, taking of the impression 76, and final assembly. All other procedures may be performed by technicians, affording significant reductions in the cost of such dental procedures. Particularly noteworthy in this regard is that the dentist need no longer locate the female portion of the attachment means within the denture subsequent to its manufacture, a procedure which previously required the expenditure of a significant amount of time on the part of the dentist. Moreover, since the female portion of the attachment means is integrally encased within the denture, rather than being separately affixed in place, the resulting interface is stronger, enhancing denture life.

After assembly, the attachment means 10 provides a means for securely retaining the denture 1 within the patient's mouth. In addition to this, the attachment means 10 of the present invention also accommodates movement of the denture 1 within the patient's mouth. This results from interaction between the stud 22, the base portion 21 and the washer 24. Both horizontal (transverse) and vertical (axial) movement are accommodated in this manner. including any movement which may be required when installing (seating) and removing the denture 1. It will also be understood that appropriate space must be made available to permit such movement. As previously mentioned, the cavity 75 developed by the lower portion 51 of the adapter 50 will automatically provide this space. It will further be understood that some limitaions on this movement will be desirable to assure the integrity of the interface developed between the attachment means 10 and the denture 1. The walls 79 defining the cavity 75 serve to automatically provide this parameter.

It will therefore be seen that the attachment means 10 and procedure for its use previously described serve well to satisfy each of the objectives previously set forth. It will also be understood that the attachment means and procedure for use previously described are capable of variation without departing from the spirit and scope of the present invention.

For example, as previously indicated, any number of attachment means 10 may be used in connection with a given dental procedure to securely retain the prosthesis in place, depending upon the teeth which remain available for use and the particular procedure which is indicated. In this regard, the attachment means 10 will find applicability not only in connection with removable prostheses as previsouly described, but also to permanent prostheses as well. Of course, in connection with these different procedures, variation in the configuration of the respective components comprising the male portion 11 and female portion 12 may be accomplished as necessary. For example, regarding the male portion 11, this could include changes in the resiliency and size of the washer 24, the diameter and length of the stud 22, the size and shape of the male member 23, and the overall configuration of the base portion 21. Regarding the female portion 12, this could include changes in the configuration of the flange 45, the size and shape of the cavity 47, and the configuration of the retention means 46. Of course, in such case, the locator/adapter 50 and positioner 65 would be accordingly modified.

It is also possible for the foregoing procedures to be used in connection with attachment means other than the attachment means 10 previously described. For example, the female portion 12 previously described may be modified by replacing the retention means 46 with a snap-ring or O-ring retention means capable of engaging the male member 23 associated with the post assembly 16. Other variations are also possible.

In this regard, while the foregoing description addresses an intra-coronal attachment, it is to be understood that the present invention will also find applicability in connection with extra-coronal attachments. One such example of this is illustrated in FIG. 10. The extra-coronal attachment means 80 illustrated again generally includes a male portion 81 and a cooperating female portion 82. The male portion 81 is again preferably associated with one of the patient's teeth 83, the female portion 82 being associated with the dental fixture, such as a partial denture 84, portions of which have been illustrated in FIG. 10. The male portion 81 includes a base 85 and a coping 86 which is attached to the base 85 and which is capable of being affixed to a prepared tooth 83, using an appropriate dental cement for example. The coping 86 is, in turn, provided with a crown 87 in conventional fashion. A post assembly 88 is provided which is capable of threadingly engaging the base 85. Essentially, the base 85 and post assembly 88 correspond to the base 15 and post assembly 16 previously described in connection with the intra-coronal attachment means 10.

The female portion 82 also essentially corresponds to the female portion 12 previously described in connection with the intra-coronal attachment means 10, but for a bracket 89 associated with the flange 90 of the female portion 82 which is capable of cooperating with the partial denture 84 in conventional manner.

Upon assembly, the male portion 81 and female portion 82 formed in accordance with the present invention will cooperate with one another, similarly to the male portion 11 and female portion 12 associated with the intra-coronal attachment means 10, to enable the partial denture 84 to be installed and removed as desired. Again, the resilient washer 24 associated with the post assembly 88 will serve to accommodate both horizontal (transverse) and vertical (axial) forces applied against the attachment means 80 during use of the partial denture 84. Assembly of the attachment means 80, as well as manufacture of the partial denture 84, would again be capable of facilitation using an appropriate locator-/adapter 50 and positioner 65 together with the procedures previously described in connection with the intra-coronal attachment means 10.

Although the foregoing description of the attachment means 10, 80 addresses a male portion engaging the patient's tooth and a female portion engaging the dental fixture, it is to be understood that the attachment means of the present invention could alternatively include a male portion which engages the dental fixure and a female portion which engages the patient's tooth, if desired in a particular application.

It will therefore be understood that various changes in the details, materials and arrangement of parts which have been herein described and illustrated in order to explain the nature of this invention may be made by those skilled in the art within the principle and scope of the invention as expressed in the following claims.

What is claimed is:

1. An attachment means for use in attaching a dental prosthesis to a tooth, comprising:
   (a) cooperating male and female portions wherein the male portion includes a base, the female portion includes a head, and the base and the head are adapted for attachment to and between the dental prosthesis and the tooth;
   (b) post assembly means including,
      (i) a base member having means for attachment to the base of the male portion, and an essentially centrally disposed aperture extending therethrough;
      (ii) a stud means extending through the aperture, one end of which incorporates universal movement means adapted for cooperation with the base member, to enable rotation of the stud means with respect to the base member;
      (iii) engagement means attached to another end of the stud means; and
      (iv) resilient washer means having an aperture extending therethrough, surrounding the stud means and separating the base member from the engagement means; and
   (c) retention means operatively associated with the head of the female portion and adapted to receive the engagement means of the stud means releasably to retain the male portion to the female portion.

2. The attachment means of claim 1 wherein the male portion is associated with the tooth and the female portion is associated with the dental prosthesis.

3. The attachment means of claim 2 wherein the base of the male portion is a cup-shaped member having a bottom adapted for attachment to the tooth, and a wall extending from the bottom and including means for engaging the base member of the post assembly means.

4. The attachment means of claim 2 wherein the head of the female portion includes a flange adapted for attachment to the dental prosthesis.

5. The attachment means of claim 1 wherein the post assembly means threadingly engages the base of said male portion.

6. The attachment means of claim 1 wherein the base member of the post assembly means has a shaped cavity for receiving the rotation means of the stud means.

7. The attachment means of claim 6 wherein the rotation means of the stud means is an essentially segmental spherical head, and the cavity of the base member is correspondingly configured to slidingly receive said head of the stud means.

8. The attachment means of claim 6 wherein the base member comprises:
   (a) an essentially flat flange having means for engagement by a tightening tool; and
   (b) a cylidrical portion depending from the flange, wherein outer face portions of the cylindrical portion include the means for attachment to the base of the male portion, and inner face portions of the cylindrical portion define the cavity for receiving the rotation means of the stud means.

9. The attachment means of claim 1 wherein one end of the stud means has a shaped aperture adapted for engagement by a tightening tool.

10. The attachment means of claim 1 wherein the stud means is threadingly attached to the engagement means.

11. The attachment means of claim 1 wherein the engagement means comprises a ball member adapted for cooperation with the retention means of the female portion, and a depending flange for engaging the resilient washer means.

12. The attachment means of claim 11 wherein the ball member includes an essentially centrally disposed aperture for receiving the end of the stud means attached thereto, and wherein terminal portions of the received end of the stud means are essentially flush with the face of the ball member.

13. The attachment means of claim 11 wherein edge portions of the ball member are shaped to receive a tightening tool.

14. The attachment means of claim 11 wherein the retention means has a shaped cavity for receiving the ball member of the engagement means.

15. The attachment means of claim 14 wherein the shaped cavity of the retention means is defined by a plurality of spaced bands depending from the head of the female portion and terminating at an inwardly directly portion which partially restricts the shaped cavity.

16. The attachment means of claim 1 wherein the resilient washer means is formed of a material which is capable of exhibiting simple hydraulic movement.

17. The attachment means of claim 16 wherein the resilient washer means is formed of silicone.

18. The attachment means of claim 16 wherein the resilient washer means biases the engagement means of the post assembly means into a normal position, and is adapted to absorb vibration.

19. For use in connection with an attachment means for attaching a dental prosthesis to a tooth, having cooperating male and female portions attachable to and between the dental prosthesis and the tooth, an improved male portion comprising:
  (a) a base means having an essentially centrally disposed aperture extending therethrough;
  (b) a stud means extending through the aperture and having adjacent one end thereof rotation means connected with the base means to enable universal movement of the stud means with respect to the base means;
  (c) means for engaging the female member, attached to another end of the stud means; and
  (d) resilient washer means operatively interposed between and separating the base means from the engagement means, and resiliently resisting universal movement of the said stud means relative to said base means.

20. The means of claim 19 further comprising retention means operatively associated with the female portion and releasably to receive the engagement means of the male portion to retain the male portion to the female portion.

21. A method for attaching a dental prosthesis to a tooth using an attachment means comprising cooperating male and female portions attachable to and between the dental prosthesis and the tooth, the male portion including a base and a post means engaging the base, and the female portion including a head and retention means associated with the head and capable of releasably engaging the post means of the male portion, said method comprising the steps of:
  (a) preparing the tooth to receive crown means;
  (b) providing crown means having the base of the male portion associated therewith;
  (c) attaching the crown means to the tooth so that the associated base extends outwardly therefrom;
  (d) providing adapter means having base means adapted for cooperation with the base of the male portion, and ball member means associated with the base means and correspondingly configured with the post means of the male portion;
  (e) positioning the base means of the adapter means over the base of the male portion;
  (f) forming an impression of the prepared tooth and the structure associated therewith;
  (g) removing the impression from the prepared tooth, developing a void in the impression in the vicinity of and corresponding to the tooth and the structure associated therewith;
  (h) attaching positioner means to the adapter means and locating the adapter means in the void of the impression, with the positioner means extending therefrom;
  (i) forming a model of the impression, enclosing the positioner means within material forming the model;
  (j) removing the model from the impression, exposing the adapter means attached to the positioner means;
  (k) attaching the retention means of the female portion to the ball member means of the adapter means;
  (l) forming the dental prosthesis in association with the model, enclosing the head of the female portion within the dental prosthesis during said forming; and
  (m) attaching the post means to the base attached to the tooth;

thereby aligning the female portion associated with the dental prosthesis with the post means associated with the male portion, permitting subsequent attachment of the male portion and the female portion.

* * * * *